United States Patent [19]
Chatterjee

[11] 3,971,379
[45] July 27, 1976

[54] ABSORBENT HYDROPHILIC CELLULOSIC PRODUCT

[75] Inventor: Pronoy Kumar Chatterjee, Spotswood, N.J.

[73] Assignee: Personal Products Company, Milltown, N.J.

[22] Filed: Apr. 4, 1975

[21] Appl. No.: 565,294

[52] U.S. Cl. ................................. 128/285; 8/120; 128/290 R; 128/290 P; 536/88; 428/212; 428/297; 428/326
[51] Int. Cl.² .......................................... A61F 13/20
[58] Field of Search ........... 428/212, 229, 274, 275, 428/288, 297, 326, 361, 393; 8/120; 128/285, 284, 290 R, 290 P; 162/146; 260/232

[56] References Cited
UNITED STATES PATENTS

| | | | |
|---|---|---|---|
| 3,241,553 | 3/1966 | Steiger | 128/156 |
| 3,521,638 | 7/1970 | Parrish | 8/120 |
| 3,526,048 | 9/1970 | Rowland et al. | 8/120 |
| 3,589,364 | 6/1971 | Dean | 128/285 |
| 3,723,413 | 3/1973 | Chaterjee et al. | 260/232 |

Primary Examiner—James J. Bell
Attorney, Agent, or Firm—J. Lipow

[57] ABSTRACT

An absorbent body is provided for use in such products as catamenial napkins and tampons, diapers, wound dressings and the like, which body incorporates hydrophilic, wet resilient, swellable, cellulosic fibers produced by a single reaction treatment of cellulose. The cellulose fibers are treated with an agent which renders the fibers hydrophilic while simultaneously crosslinking them with a crosslinking radical having the structure:

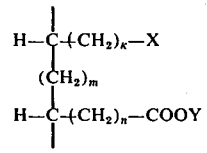

where X is chosen from the group consisting of H or COOY: Y is chosen from the group consisting of Na, K, Li, Ce or H; and $k$, $m$ and $n$ are integers ranging from 0 to 4.

15 Claims, 8 Drawing Figures

U.S. Patent   July 27, 1976   3,971,379
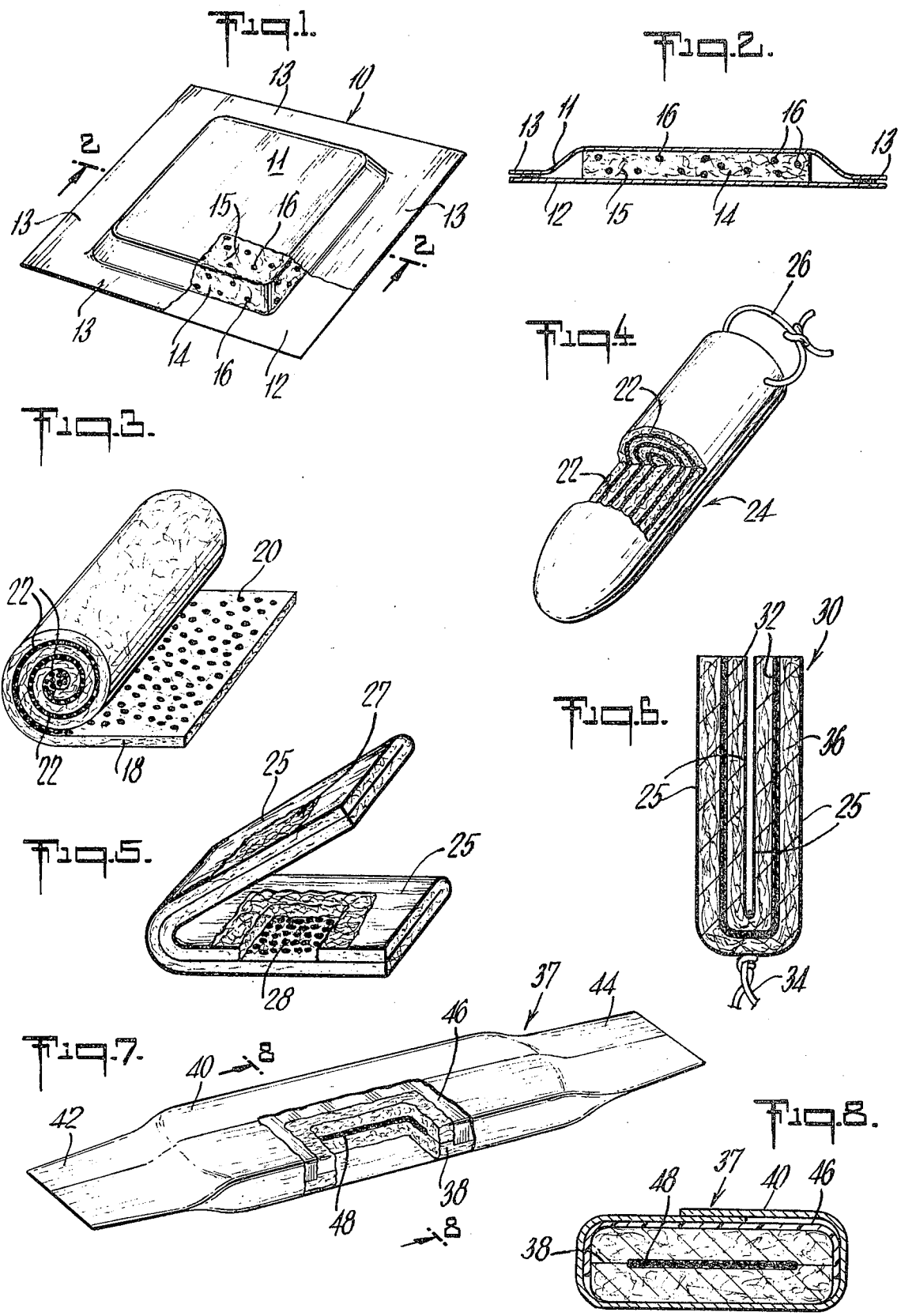

ABSORBENT HYDROPHILIC CELLULOSIC PRODUCT

BACKGROUND OF THE INVENTION

This invention relates to absorbent products and particularly to such products provided for absorbing body fluids, as for example, catamenial napkins, tampons, diapers, wound dressings and the like. Specifically, this invention relates to employing, as an absorbent media in such products, cellulose fibers which have been crosslinked with a specific class of crosslinking agents and which have the properties of high absorbency and retention of body fluids.

Cellulose has long been used as an absorbent material for absorbing body fluids in that it is a cheap, abundant and relatively absorbent material. This notwithstanding, the art has searched for improvements in the absorptivity of cellulose in an effort to reduce the bulk of absorbent products or to reduce their cost and several suggestions have already been made proposing that cellulose be chemically modified to achieve these goals.

One such proposal is found in U.S. Pat. No. 3,241,553 issued to Fred H. Steiger on Mar. 22, 1966 wherein it is disclosed that the absorption and retention capacity of absorbent products utilizing cellulosic fibers may be increased by first crosslinking the fibers. As is described in this patent, the crosslinking greatly increases the resiliency of a body of fibers in the wet state thereby increasing the interstitial volume between fibers and hence, the volume of fluid which can be held therein. The crosslinking, however, does not increase the quantity of fluid held within a fiber, this being dependent on the basic hydrophilicity of the starting cellulosic itself. Thus, from the teaching of this reference, crosslinking will increase the absorbency of both hydrophilic and relatively hydrophobic cellulosics. This teaching has been applied in U.S. Pat. No. 3,589,364 issued to Walter Lee Dean, et al. on June 29, 1971. Disclosed therein is highly absorbent cellulosic fibers comprising the product of two chemical reactions, to wit: the carboxymethylation of cellulose wherein hydroxyl groups on the anhydroglucose units in the cellulose chain are carboxymethylated to a high degree of substitution and the crosslinking of the cellulosic chains. Produced is an insoluble, fibrous mass which, by virtue of the crosslinking, maintains its fibrous integrity and hence, has a high interstitial volume and a high interfiber capacity for fluids and which, by virtue of the inherent hydrophilicity of carboxymethylated cellulose, has a high intrafiber absorption capacity.

Unfortunately, while the aforementioned hydrophilic crosslinked fibers represent a great improvement over unmodified cellulose, complex processing is required to obtain these properties. Basically, two separate chemical reactions must be carried out, the carboxymethylation and the crosslinking. Thus, two reagents are involved and the product of reactions must be washed free of both of these reagents. In view of the complexity of the process required to produce such an absorbent fiber, the ultimate cost to the consumer of products incorporating such fibers is high and much of the advantages in substituting such fibers for unmodified cellulose is lost.

SUMMARY OF THE INVENTION

In accordance with this instant invention, an absorbent body is provided for use in such absorbent products as catamenial napkins and tampons, diapers, wound dressings, and the like which absorbent body incorporates hydrophilic, wet resilient swellable cellulosic fibers which may be produced by a single reaction treatment of cellulose, thereby overcoming the drawbacks associated with prior such fibers. More specifically, in accordance with this invention, an absorbent body is provided with fibers of crosslinked cellulose, said cellulose being crosslinked with an oxygen atom of a hydroxy group in an anhydroglucose unit of one cellulose molecule linked to an oxygen atom of a hydroxy group in an anhydroglucose unit of a second cellulose molecule through a crosslinking radical having the structure:

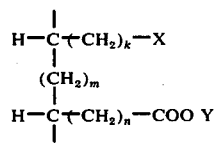

where X is chosen from the group consisting of H or COOY; Y is chosen from the group consisting of Na, K, Li, Ce or H; and $k$, $m$ and $n$ are integers ranging from 0 to 4. A satisfactory product is obtained when the degree of crosslinking results in as little as 0.005 moles of crosslinking radical per mole of anhydroglucose unit is present in the crosslinked fibers. Preferably, the degree of crosslinking should correspond to at least 0.015 moles of crosslinking radical per mole of anhydroglucose unit. In order to obtain a satisfactory hydrophilic fiber, it is necessary to choose a crosslinking radical such that, in combination with the above stated degree of crosslinking requirements, there are at least 0.3 moles of —COO(alkalai) in the crosslinking radical per anhydroglucose unit and preferably at least 0.4 moles per anhydroglucose unit. To avoid a loss of fibrous integrity upon wetting, it is desirable that this parameter does not exceed a value of 1.6 moles per anhydroglucose unit. An excellent working range for this parameter is from 0.5 to 1.0.

BRIEF DESCRIPTION OF THE DRAWINGS

In the drawings:

FIG. 1 is a perspective view of an absorbent dressing or a disposable diaper embodying this invention, a portion thereof being broken away to show interior detail;

FIG. 2 is a cross-sectional view of the dressing or diaper of FIG. 1 taken along line 2—2;

FIG. 3 is a perspective view of a partially rolled blank for compressing into a first catamenial tampon embodying this invention;

FIG. 4 is a perspective view of a finished tampon made from the blank of FIG. 3, a portion thereof being broken away to show interior detail;

FIG. 5 is a perspective view of a partially folded blank for compressing into a second catamenial tampon embodying this invention;

FIG. 6 is a cross-sectional view of the finished tampon made from the blank of FIG. 5 taken through an axial plane through the tampon;

FIG. 7 is a perspective view of a catamenial sanitary napkin embodying this invention, a portion thereof being broken away to show interior detail; and FIG. 8 is a cross-sectional view of the sanitary napkin of FIG. 7 taken along line 8—8.

DESCRIPTION OF THE INVENTION

The starting cellulose may be any of the natural or regenerated forms of cellulose now commonly used in absorbent products and may be in any form. For example, wood flour, wood pulp, cotton fibers, rayon fibers and the like are all suitable for use in accordance with this invention. It is preferred, however, that the cellulose be in fibrous form as this form is best integrated into absorbent products, with wood pulp fibers being the fiber of choice. Preferably, such fibers have an average length of from 0.5 mm to 3.0 mm.

The fibers are crosslinked by combining them, in a suitable dispersing medium with crosslinking agents of the type comprising dihalogenated mono-, or dihalogenated di-, carboxylic acids and the alkaline salts thereof with chlorine and bromine halogenation being preferred. Examples of suitable dihalogenated monocarboxylic acids and salts are dibromopropionic acid, dichloro butyric acid, dichlorovaleric acid, dichloro trimethyl acetic and di bromo caproic acid and the sodium, potassium cesium, or lithium salts thereof. Examples of suitable dihalogenated di carboxylic acids are di bromo malonic acid, dichloro succinic acid, di bromo glutaric acid and di bromoadipic acid and the sodium, potassium, lithium and cesium salts thereof.

In accordance with the teachings of this invention, the crosslinking agent must act difunctionally, i.e., must form a bridge between adjacent cellulose molecules. It is preferred then that the halogen atoms of the crosslinking agent be substituted on different carbon atoms. This is primarily because the reactivity of these groups decreases as the distance between them decreases and accordingly, a dihalo crosslinking agent having the halogen groups both substituted onto the same carbon atom is not very reactive.

A suitable dispersing medium for the mixture of cellulose and crosslinking agents is generally one which is compatible with the reagents and in which the crosslinking agent is soluble. Suitable media are, for example, water, methanol, ethanol, propanol or the like.

The reaction of these crosslinking agents is accelerated with the use of alkaline catalyst such as aqueous solutions of sodium hydroxide for example, which are likewise incorporated into the reaction mixture. The reaction mixture is then heated to complete the crosslinking reaction and then filtered. The resulting filtrate is washed and dried to obtain the hydrophilic crosslinked cellulose of this invention.

In accordance with the teachings of this invention, the degree of crosslinking is controlled to provide at least 0.005 moles of crosslinking radical per mole of anhydroglucose unit, and in combination with this criteria, the quantity and kind of crosslinking agent is controlled to provide at least 0.3 moles of —COO(alkalai metal) groups per anhydroglucose unit. The degree of crosslinking and the quantity of —COO(alkalai metal) groups per anhydroglucose unit can be controlled by selecting a combination of specific reaction conditions from the plurality of independent variables controlling the reaction system. For example, once a specific crosslinking agent has been chosen, the major independent variables are the ratio of reagents to cellulose in the reaction mixture, the concentration of reagents in the reaction mixture (best expressed on a cellulose-free basis), the temperature at which the reaction is carried out, and the duration of the heating period. It is well understood in the art that, in general, the selection of high values for all of these variables will result in increasing the degree of crosslinking and the quantity of —COO(alkalai metal) groups per anhydroglucose unit.

The ratio of crosslinking agent to cellulose has been found to be satisfactorily varied from 0.005–3 moles of reagent per mole of anhydroglucose unit. A suitable operating concentration of the crosslinking agent in the reaction mixture (on a cellulose free basis) may vary from 1 to about 30% by weight. Suitable temperatures at which the reaction mixture may be heated can vary from 25°C to just below the boiling temperature of the reaction solution, and the reaction may be carried out for a period of time of from 0.5 to as much as 24 hours.

The hydrophilic crosslinked cellulose of this invention can be used as an absorbent media in such products for absorbing body fluids as sanitary napkins, tampons, and diapers and can be incorporated into absorbent bodies, as are used in these products in combination with other absorbent material such as untreated cellulose, rayon or other hydrophilic polymers.

Referring now to the drawings, in FIGS. 1 and 2, an absorbent dressing or disposable diaper 10 is provided with a body fluid pervious facing sheet 11 which can be, for example, gauze, tissue or a nonwoven fabric. A body fluid-impermeable backing sheet 12 is provided preferably made of a thin-gauge polyolefin or polyester sheet such as a polyethylene or polyethylene terephthalate film. It will be understood by one skilled in the art that the impermeable backing sheet is used where a dry surface is required such as in a diaper or dressing. In circumstances where this is not necessary, such as in a surgical sponge, the backing sheet may be of a permeable material such as, for example, the same material as the facing sheet. The facing and backing sheets are adhered together along common edges 13 with a suitable, preferably water-insoluble, adhesive or may alternatively be heat-sealed if thermoplastic materials are used in the sealing area. Sandwiched between the facing sheet 11 and the backing sheet 12 is an absorbent body 14 in the form of a planar pad made of absorbent fibers 15 such as unmodified cellulosic fibers, e.g., wood pulp, rayon or the like. In accordance with this invention, dispersed throughout this absorbent layer 14 are particles 16 of the hydrophilic crosslinked cellulose of this invention and the resulting absorbent body 14 then has a capacity for absorbing and retaining body fluids which greatly exceeds a body of equal weight composed entirely of wood pulp.

A second embodiment of this invention is shown in FIGS. 3 and 4 of the drawings. Shown in FIG. 3 is an elongated pad 18 of absorbent material such as rayon fibers having a generally rectangular shape and illustrated as formed into a cylinder by rolling from one end to the other in a direction parallel to the longitudinal sides of the pad. In accordance with this invention, prior to rolling, a thin layer 20 of the hydrophilic crosslinked cellulose material is applied to the surface of the rectangular pad so that upon rolling, the layer forms strata 22 of the crosslinked cellulose alternating with the rayon as viewed in the radial cross-section. The rolled pad is then compressed in a die to the desired tampon shape 24 as is illustrated in FIG. 4. The tampon is provided with the usual withdrawal string 26 which may be sewn through the removal end of the tampon or applied by other means known in the art, such as being looped or tied around the rectangular pad 18 prior to rolling.

FIGS. 5 and 6 illustrate still another embodiment of this invention in a catamenial tampon. A rectangular pad 27 of wood pulp laid upon a porous nonwoven cellulosic fabric cover 25 has a layer 28 of the herein prescribed hydrophilic crosslinked cellulose applied to one surface. The pad 27 with the nonwoven cover 25 is then folded about its longitudinal center and folded once more into a U-shaped blank, as illustrated in FIG. 5. The blank is then placed in a cylindrical die and compressed radially and/or longitudinally into the desired tampon shape 30 as shown in FIG. 6. A withdrawal string 34 is provided at the withdrawal end of the compressed tampon 30 and may be attached in a manner similar to that described above, i.e., sewn on, looped or tied around the pad 27 prior to folding etc. The finished tampon 30 will then comprise centrally located strata or cores of crosslinked cellulose 32 surrounded and held in place by compressed layers of wood pulp 36 which in turn are held in place by the nonwoven cover. The tampon will be substantially more absorbent than one of similar construction and weight composed entirely of wood pulp. In addition to the simple structure of this tampon, an added advantage is that the most absorbent material, the cores 32 of hydrophilic crosslinked cellulose, are within the tampon thus creating a positive driving force for liquid absorption directed toward the interior. Accordingly, the tampon tends to collect absorbed liquid in the cores, leaving the outer layer relatively dry, thereby decreasing the likelihood of surface puddling or expulsion of fluid under the occasional stresses placed on the tampon when worn.

FIGS. 7 and 8 illustrate the invention embodied in a sanitary napkin 37. An absorbent pad 38 comprised of, for example, wood pulp is enveloped by a liquid permeable wrapper 40 which extends at both ends beyond the pad so as to provide attachment tabs 42 and 44. A liquid impermeable sheet 46 is sandwiched, on one surface of the pad, between the pad and the wrapper and may extend, at least partially over the sides of the pad. The impermeable sheet may be, for example, a polyethylene film. In a central portion of the pad 38, there is interposed a layer 48 of the herein prescribed hydrophilic crosslinked cellulose.

It will be appreciated by one skilled in the art that the methods of incorporating the hydrophilic crosslinked cellulose of this invention into the specific absorbent bodies are to a large measure interchangeable and for example, the dressing or diaper of FIGS. 1 and 2 may be provided with a central core such as is shown for the sanitary napkin of FIGS. 7 and 8. Likewise, the tampons of FIGS. 3–6, as well as the napkin of FIGS. 7 and 8 may have the hydrophilic crosslinked cellulose distributed throughout their respective absorbent bodies, as is shown for the dressing or diaper of FIGS. 1 and 2.

The relative quantities of hydrophilic crosslinked cellulose which may be incorporated into the absorbent bodies of this invention may vary widely depending upon the properties desired for the finished product. An increase in the quantity will generally produce a more absorbent product but will also increase the difficulty of manufacturing the same and will certainly increase the cost of the product. In general, for the products described herein, it is desirable to incorporate from about 2 to about 50 percent by weight of the hydrophilic crosslinked cellulose, based on a total weight of the absorbent body and preferably about 5 to about 30 percent.

The present invention will be understood more fully by reference to the following examples.

EXAMPLE 1

A slurry of 5 grams of southern pine kraft wood pulp fluff is prepared by dispersing the fluff in 133 ml. of isopropanol. To this slurry is added 40 gms. of a 23% by weight aqueous sodium hydroxide solution and the mixture is stirred for 30 minutes at room temperature. A crosslinking agent consisting of 17.5 g. of 2,3-dibromosuccinic acid is next added and the mixture is further stirred at room temperature for 30 minutes. The resulting mixture is next heated in an oven at a constant temperature of 55°C for 3½ hours. The mixture is then filtered and the fibers obtained are washed at room temperature with 70 percent methanol and then Soxhlet extracted with methanol by refluxing for a period of 6 hours. The resulting fibers, now purified with respect to the crosslinking reagents, comprise cellulose chains having an oxygen atom in one anhydroglucose unit of one cellulose molecule crosslinked to an oxygen atom in an anhydroglucose unit of a second cellulose molecule through a crosslinking radical having the following structure:

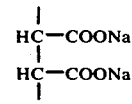

The degree of crosslinking is about 0.15 moles of crosslinking radical per anhydroglucose unit and there are approximately 0.5 moles of COONa groups per anhydroglucose unit.

EXAMPLE 2

A slurry of 5 grams of southern pine kraft wood pulp fluff is prepared by dispersing the fluff in 133 mil of isopropanol. To this slurry is added 40 gms. of a 23% by weight aqueous sodium hydroxide solution and the mixture is stirred for 30 minutes at room temperature. A crosslinking agent consisting of 17.5 gms. of 2,2'-dibromoadipic acid is next added and the mixture is further stirred at room temperature for 30 minutes. The resulting mixture is next heated in an oven, at a constant temperature of 55°C for 3½ hours. The mixture is then filtered and the fibers obtained are washed at room temperature with 70 percent methanol and then Soxhlet extracted with methanol by refluxing for a period of 6 hours. The resulting fibers, now purified with respect to the crosslinking reagents, comprises cellulose chains having an oxygen atom in an anhydroglucose unit of one cellulose molecule crosslinked to an oxygen atom in an anhydroglucose unit of a second cellulose molecule through a crosslinking radical having the following structure:

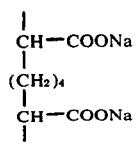

The degree of crosslinking is about 0.15 moles of crosslinking radical per anhydroglucose unit and there are approximately 0.5 moles of COONa groups per anhydroglucose unit.

EXAMPLE 3

The product of Example 1 is tested for its ability to absorb and retain a 1% by weight aqueous NaCl solution (this approximating the salinity of such body fluids as menstrual fluid and urine) and a solution of water containing 0.2% of a surface active agent to emulate the surface tension of body fluids (approximately 40 dynes/cm.) The surface active agent used is a poly-(ethylene oxide)-poly(propylene oxide) block copolymer sold by the Wyandette Chemical Corporation of Michigan, U.S.A., under the trade name Pluronic. The testing method employs the Porous Plate Testing Apparatus and is described in detail in Textile Res., J., 37, pp 356–366, 1967. Briefly, this test involves placing a sample of a given absorbent material in what is essentially a Buckner funnel having a porous bottom plate and holding the sample in place by applying a standard weight thereto to standardize the confining pressure under which absorption and retention is to be measured. For this example, a confining pressure of 5 gm/cm² was employed. The porous plate is brought in contact with a reservoir of fluid and the sample is allowed to absorb fluid through the porous plate. With the sample at the level of the reservoir, the fluid absorbed is subjected to essentially a zero hydraulic head with respect to the reservoir. The apparatus is provided with means for directly measuring the volume of fluid absorbed. To determine fluid retention capacity, the saturated sample is elevated, with respect to the fluid reservoir, thereby imposing a hydraulic head upon the fluid absorbed which, in the case of this example, is chosen as 35.5 cm. of water. The apparatus is provided with means for directly measuring the volume of fluid retained under this hydraulic head, from which the retention capacity is calculated as the volume of fluid retained per unit weight of absorbent material. In addition to testing the material obtained from the method of Example 1, a sample of untreated wood pulp as well as a sample of wood pulp which has been crosslinked with formaldehyde in accordance with the teachings found in the above mentioned U.S. Pat. No. 3,241,553 are tested. The results of these tests are reported in the Table following.

FLUID RETENTION CAPACITY BY POROUS PLATE METHOD

Fluids: Water with 0.2% Pluronic and 1% aqueous NaCl solution
Confining Pressure: 5g/cm²
Hydrostatic Head: 35.5 cm water

| Sample | Fluid Retention Capacity (cc/g) | |
|---|---|---|
| | Water | Saline Solution |
| Untreated Wood Pulp | 2.4 | 2 |
| Wet Crosslinked Wood Pulp | 2.6 | 1–2 |

FLUID RETENTION CAPACITY BY POROUS PLATE METHOD

Fluids: Water with 0.2% Pluronic and 1% aqueous NaCl solution
Confining Pressure: 5g/cm²
Hydrostatic Head: 35.5 cm water

| Sample | Fluid Retention Capacity (cc/g) | |
|---|---|---|
| | Water | Saline Solution |
| Material from Example 1 | 10.5 | 5.2 |

As the above data clearly shows, the untreated wood pulp as well as the crosslinked wood pulp both exhibit essentially the same fluid retention capacity for water and saline solution. In marked contrast thereto, the material of Example 1, made in accordance with the teachings of this invention exhibited a dramatically higher fluid retention capacity.

What is claimed is:

1. An absorbent body comprising hydrophilic crosslinked cellulose, said cellulose being crosslinked with an oxygen atom of a hydroxy group in an anhydroglucose unit of one cellulose molecule linked to an oxygen atom of a hydroxy group in an anhydroglucose unit of a second cellulose molecule through a crosslinking radical having the structure:

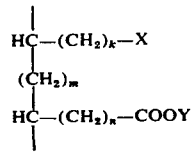

where X is chosen from the group consisting of H or COOY; Y is chosen from the group consisting of Na, K, Li, Ce, or H; and k, m and n are integers ranging from 0 to 4.

2. The absorbent body of claim 1 wherein said hydrophilic crosslinked cellulose has a degree of crosslinking of at least 0.005 moles of crosslinking radical per mole of anhydroglucose unit.

3. The absorbent body of claim 2 wherein said hydrophilic crosslinked cellulose has a degree of crosslinking of at least 0.015 moles of crosslinking radical per mole of anhydroglucose unit.

4. The absorbent body of claim 1 wherein said hydrophilic crosslinked cellulose has at least 0.3 moles of —COO(alkalai metal) groups in the crosslinking radical per mole of anhydroglucose unit.

5. The absorbent body of claim 4 wherein said hydrophilic crosslinked cellulose has at least 0.4 moles —COO(alkalai metal) groups in the crosslinking radical per mole of anhydroglucose unit.

6. The absorbent body of claim 1 wherein said crosslinking radical has the structure:

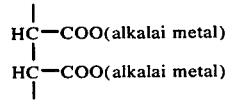

7. The absorbent body of claim 1 wherein said crosslinking radical has the structure:

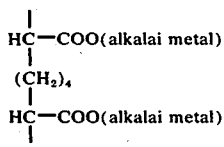

8. A catamenial device comprising an absorbent body of first absorbent material and hydrophilic crosslinked cellulose, said cellulose being crosslinked with an oxygen atom of a hydroxy group in an anhydroglucose unit of one cellulose molecule linked to an oxygen atom of a hydroxy group in an anhydroglucose unit of a second cellulose molecule through a crosslinking radical having the structure:

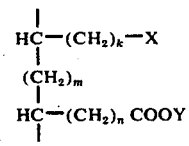

where X is chosen from the group consisting of H or COOY, Y is chosen from the group consisting of Na, K, Li, Ce, or H; and $k$, $m$ and $n$ are integers ranging from 0 to 4.

9. The device of claim 8 wherein said hydrophilic crosslinked cellulose is substantially uniformly distributed in the absorbent body.

10. The device of claim 9 wherein said absorbent body comprises at least one core of said hydrophilic crosslinked cellulose.

11. The device of claim 10 wherein said absorbent body comprises a plurality of cores of said hydrophilic crosslinked cellulose, said cores being separated by said first absorbent material.

12. The device of claim 11 wherein said first absorbent material is cellulose fibers.

13. A tampon comprising the device of claim 11 wherein said absorbent body comprises a pad of said first absorbent material having a layer of said hydrophilic crosslinked cellulose thereon, said pad being rolled into cylindrical form and compressed into the final tampon shape.

14. A sanitary napkin comprising the device of claim 8 wherein said absorbent body is in the form of a planar pad sandwiched between a backing sheet and a facing sheet, at least one of which is menstrual fluid permeable.

15. The napkin of claim 14 wherein both sheets are fluid permeable and form a continuous cover sheet enveloping the absorbent body.

* * * * *